United States Patent
Ryu

(10) Patent No.: US 10,959,711 B2
(45) Date of Patent: Mar. 30, 2021

(54) METHOD AND APPARATUS FOR SELF-COLLECTING INTRAVAGINAL SAMPLE FOR HPV TEST

(71) Applicant: Sang Young Ryu, Seoul (KR)

(72) Inventor: Sang Young Ryu, Seoul (KR)

(*) Notice: Subject to any disclaimer, the term of this patent is extended or adjusted under 35 U.S.C. 154(b) by 771 days.

(21) Appl. No.: 15/317,288

(22) PCT Filed: Jun. 3, 2015

(86) PCT No.: PCT/KR2015/005547
§ 371 (c)(1),
(2) Date: Dec. 8, 2016

(87) PCT Pub. No.: WO2015/190738
PCT Pub. Date: Dec. 17, 2015

(65) Prior Publication Data
US 2017/0112478 A1    Apr. 27, 2017

(30) Foreign Application Priority Data

Jun. 10, 2014  (KR) .................... 10-2014-0070210
Sep. 15, 2014  (KR) .................... 10-2014-0122165
Oct. 15, 2014  (KR) .................... 10-2014-0139308

(51) Int. Cl.
*A61B 10/02*  (2006.01)
*C12M 1/26*  (2006.01)
*A61B 10/00*  (2006.01)

(52) U.S. Cl.
CPC ...... *A61B 10/0291* (2013.01); *A61B 10/0045* (2013.01); *A61B 10/02* (2013.01);
(Continued)

(58) Field of Classification Search
CPC ........ A61B 2010/0074; A61B 10/0045; A61B 10/02
See application file for complete search history.

(56) References Cited

U.S. PATENT DOCUMENTS 3,298,369 A * 1/1967 Pirie .............. A61F 5/4553
                                                        604/330
4,327,744 A    5/1982 Smith
(Continued)

FOREIGN PATENT DOCUMENTS

CN    1539392 A    10/2004
CN    1827049 A     9/2006
(Continued)

OTHER PUBLICATIONS

International Search Report and Written Opinion for PCT App No. PCT/KR2015/005547 dated Jul. 21, 2015, 14 pgs.
(Continued)

*Primary Examiner* — Christian Jang
*Assistant Examiner* — Karen E Toth
(74) *Attorney, Agent, or Firm* — Procopio, Cory, Hargreaves & Savitch LLP

(57) ABSTRACT

The present invention relates to a method for self-collecting intravaginal sample for HPV test. The self-collecting intravaginal sample apparatus of the present invention comprises: an open end part, a closed end part, a tube providing an inner space that a finger could enter to insert an apparatus into women's vagina, a collecting part collecting intravaginal sample and attached outer surface of the closed end of the tube, and a turner preventing the collecting part being contaminated from an outer contaminant; wherein the collecting part collects a sample from the vagina by turning over the tube inside out so that collecting part may place inside of the tube.

10 Claims, 15 Drawing Sheets

(52) U.S. Cl.
CPC ....... *C12M 1/26* (2013.01); *A61B 2010/0006* (2013.01); *A61B 2010/0074* (2013.01)

(56) References Cited

U.S. PATENT DOCUMENTS

| | | | | |
|---|---|---|---|---|
| 4,920,974 | A | * | 5/1990 | Roth .................. A61B 10/0291 600/572 |
| 4,991,592 | A | * | 2/1991 | Christ .................. A61B 42/10 600/567 |
| 2002/0107497 | A1 | * | 8/2002 | Osborn, III ......... A61F 13/2051 604/385.18 |
| 2002/0161313 | A1 | * | 10/2002 | Sak .................. A61B 10/0045 600/569 |
| 2003/0120180 | A1 | * | 6/2003 | Kaylor ................ A41D 13/087 600/584 |
| 2004/0153000 | A1 | | 8/2004 | Pevoto |
| 2005/0288606 | A1 | * | 12/2005 | Alter .................. A61B 10/0291 600/572 |
| 2006/0260021 | A1 | * | 11/2006 | Kerr-Maddox .... A41D 19/0034 2/159 |
| 2012/0116356 | A1 | | 5/2012 | Davenport |
| 2014/0377796 | A1 | * | 12/2014 | Yan .................... G01N 33/5005 435/34 |

FOREIGN PATENT DOCUMENTS

| | | |
|---|---|---|
| CN | 101869491 A | 10/2010 |
| JP | 4969270 B2 | 7/2012 |
| KR | 20-0211753 Y1 | 1/2001 |
| KR | 10-2003-0085096 A | 11/2003 |
| KR | 10-0671825 B1 | 1/2007 |
| KR | 10-1141256 B1 | 5/2012 |
| KR | 20-0469480 Y1 | 10/2013 |

OTHER PUBLICATIONS

Extended European Search Report for PCT/KR2015/005547 dated Jan. 5, 2018, 7 pages.

Communication pursuant to Article 94(3) EPC for related European Application No. 15807446.8 dated Mar. 11, 2020 (6 pages).

* cited by examiner

METHOD AND APPARATUS FOR SELF-COLLECTING INTRAVAGINAL SAMPLE FOR HPV TEST

CROSS-REFERENCE TO RELATED APPLICATIONS

This application is a U.S. National Stage entry of PCT Application No. PCT/KR2015/005547, filed on Jun. 3, 2015, which claims priority to KR Application No. 10-2014-0139308, filed Oct. 15, 2014, KR Application No. 10-2014-0122165, filed Sep. 15, 2014 and KR Application No. 10-2014-0070210, filed Jun. 10, 2014. The contents of the foregoing are incorporated by reference.

BACKGROUND OF THE INVENTION

The present invention disclosed herein relates to an apparatus for HPV test, but in more detail it relates to a method and apparatus for self-collecting intravaginal sample for HPV test by inserting an apparatus herself.

Human papilloma virus; HPV has been a main cause of the uterine cervical cancer. The uterine cervical cancer is the fourth most frequent cancer by 10.1% among frequent cancer caused in women and when it includes epithelium cancer, it takes the first cancer as 22.3%. Every year, over 7,000 patients are occurred from this cancer and it is the most important cancer among Korean women as it occurs for 26.5 subject women out of 10,000 subject women. To decrease death rate caused by the uterine cervical cancer, an early diagnosis is required. Typical method to test uterine cervical test is a pap smear, which inserts a tool such as swab or cyto-brush into woman's vagina to collect sample, or a traditional method colposcopy. Although there are so many disadvantages of these methods there is no other method so these methods has been used until now.

However, since cervical cancer HPV test can only be tested by vising obstetrics and gynecology, a lot of women especially young women feel shame so they hesitate to take HPV test which leads to missing an early treatment. Also, when inserting a sample collecting apparatus in women's vagina could damage inner wall of the vaginal or cause pain by stimulating inner wall of the vaginal. After collecting sample from the vagina and during taking out the sample outside of the vagina, it could contaminate the collected sample by other secretion of inner side of the vagina.

SUMMARY OF THE INVENTION

An embodiment of the present invention is to provide to a method and an apparatus for self-collecting intravaginal sample for HPV test by inserting an apparatus woman herself.

An embodiment of the present invention is to provide to a method and an apparatus for self-collecting intravaginal sample for HPV test to prevent contamination of a sample after collecting the sample.

The objects of the inventive concept are not limited to the above mentioned descriptions. Other objects thereof will be understandable by those skilled in the art from the following descriptions.

According to an aspect of the present invention, the vaginal sample self-collecting apparatus comprises: a tube providing an inner space that a finger could enter to insert an apparatus into women's vagina and comprising a latter end having an open end part and a front end having a closed end part; and a collecting part that collects sample of the vagina, wherein the collecting part is provided at an outer surface of the closed end part of the tube.

Also, the apparatus for self-collecting intravaginal sample further comprises a turner to prevent the collecting part being contaminated from an outer contaminant by turning over the tube inside out so that the collecting part which collects a sample from the vagina may place inside of the tube.

Also, the turner comprises a pull string, wherein one end of the pull string is attached inner surface of the closed end part of the tube and the other end of the pull string is installed as exposed to the outside through an open end part of the tube.

Also, the turner may comprise a flow channel, wherein the flow channel provides a moving path for the sample to be provided to a diagnosis apparatus.

Also, the turner comprises a flexible hose that the flow channel is formed, wherein the flexible hose comprises a flow part and a leak part, wherein the flow part connects the flow channel and the closed end part of the tube, wherein the leak part is exposed to outside through the open end part of the tube. The leak part may be blocked.

Also, the collecting part may comprise a bumpy surface which is formed at the outer surface of the closed end part of the tube.

Also, the tube may further comprise an extension part which prevents friction between a finger and the tube so that the front end may turn inside out when taking out the finger, wherein the extension part places in between the front end and the latter end.

Also, the extension part may have wider area than the front end.

Also, the extension part may have at least one wrinkle.

Also, the front end may have relative higher flexibility and elasticity than the extension part.

Also, the tube may further comprise a tight band and a sealed member, wherein the sealed member is provided at circumference of the open end part.

Also, the tube may be composed of at least one of natural rubber, synthetic rubber, and silicon.

Also, the apparatus may further comprise a protective cover, wherein the protective cover encases the tube and protects the collecting part from the outer contaminants when it is inserted inside of the women's vagina. At the closed end part of the protective cover, a tear line may be formed.

According to an aspect of the present invention, the method for self-collecting sample of a vagina comprises: a inserting step inserting a finger in the tube then inserting the tube into women's vagina, wherein the tube has the open end part and the closed end part; a collecting step collecting a sample of vagina from the collecting part by using the finger that is inserted in the tube, wherein the collecting part is attached outer surface of the end part of the tube; a turnover step turning over inside out of the tube to place the colleting part inside of the tube and to prevent contaminating the collecting part from outside contaminants, wherein the collecting part has already collected the sample of the vagina.

Also, the turnover step turns over inside out of the tube by pulling the pull string after taking out a finger, wherein the tube is inserted in women's vagina, and wherein one end of the pull string is attached inner surface of the closed end of the tube.

Also, a sealing step may further be comprised, wherein the sealing step seals the open end part of the tube after the turnover step.

Also, an injecting step may further be comprised, wherein the injecting step injects a fixing solution inside of the tube to prevent deformation of the sample, after the turnover step.

Also, the collecting part may comprise a signal color material that could be identified by the naked eye in reacting to HPV.

According to an embodiment of the present invention, the apparatus for self-collecting intravaginal sample has particular effects which are: promoting user's convenience as it is easier for woman to collect a sample from her vagina; and increasing reliability of HPV test as we can treat a collected sample more sanitarily.

According to an embodiment of the present invention, there is a particular effect that we can easily provide the collected sample to a diagnosis apparatus.

DETAILED DESCRIPTION

The present invention may apply variety changes and have many embodiments. Certain embodiments are indicated in drawing and explained in detailed explanations. However, the present invention is not meant to be limited in certain embodiments, it should be understood that the present invention includes all the changes, equivalents, and alternatives. When explaining the present invention detailed descriptions of the prior art may be omitted when it is determined that it clouds the important points of the invention.

The words used in this application are to explain certain embodiments and it is not meant to limit the present invention. Singular forms include plural forms as well, unless the context clearly indicates otherwise. The terms "comprise" or "have," etc. of the application is to specify the presence of stated features, integers, steps, operations, elements, and/or components, but do not preclude the presence or addition of one or more other features, integers, steps, operations, elements, components, and/or groups thereof.

The first terms or second terms, etc. may be used to explain variety components, but the components should not be limited by the terms. The above terms are only used to differentiate a one component from the other components.

Various example embodiments will be described more fully hereinafter with reference to the accompanying drawings. In explaining embodiments referring to attached drawings, components which are the same or corresponding to each other regardless of drawing number have the same reference number and the duplicate explanations may be omitted.

The First Embodiment

Figure 1:
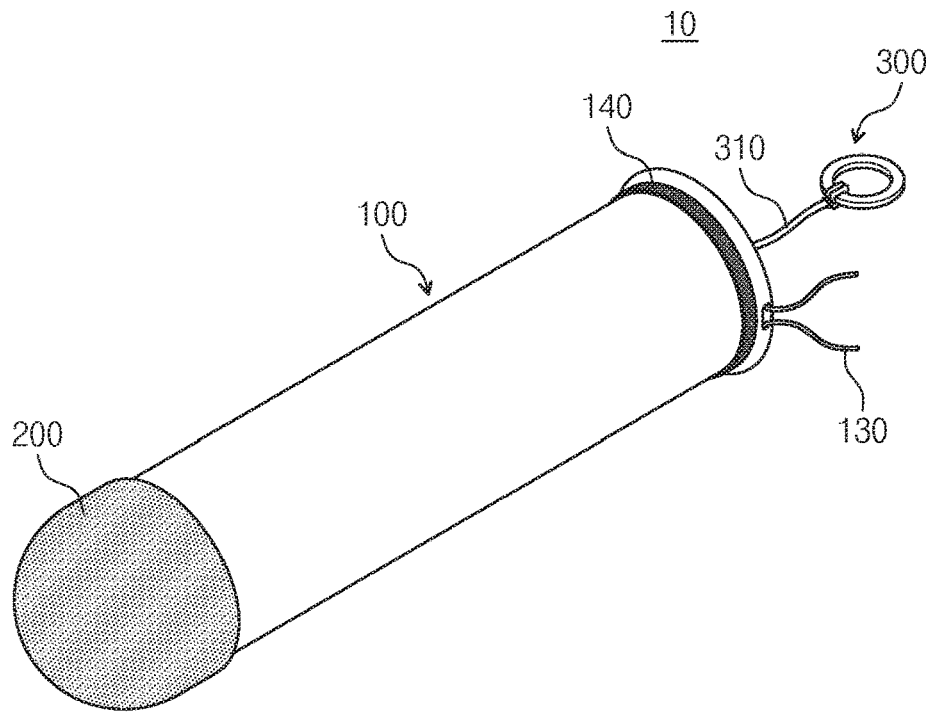
FIG. 1 is a perspective view of an apparatus for self-collecting intravaginal sample in accordance with the first embodiment of the present invention.
Figure 2:
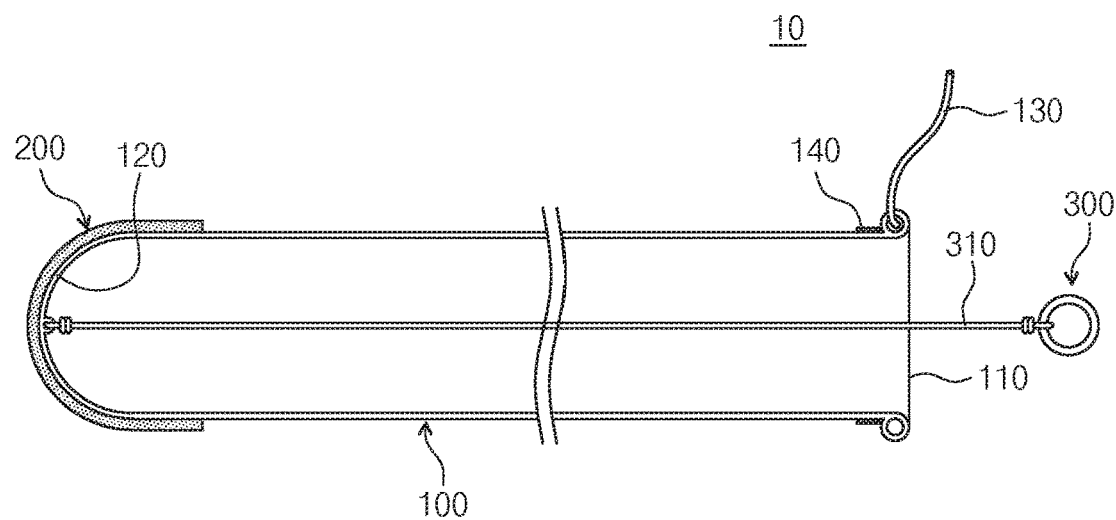
FIG. 2 is a plan view of an apparatus for self-collecting intravaginal sample in accordance with the first embodiment of the present invention.

FIG. 1 is a perspective view of an apparatus for self-collecting intravaginal sample in accordance with the first embodiment of the present invention. FIG. 2 is a plan view of an apparatus for self-collecting intravaginal sample in accordance with the first embodiment of the present invention.

Referring to FIGS. 1 and 2, the apparatus for self-collecting intravaginal sample 10 comprises a tube 100, a collecting part 200, and a turner 300.

The tube 100 has an open end part 110 and a closed end part 120, and provides an inner space where a finger may enter so that the tube can insert inside of woman's vagina. The tube 100 is to pass through a passage of an inner side of a vagina so that the closed end part 120 of the tube can reach a cervix. Therefore, the tube 100 may be a cylinder structure that is easily inserted in inner side of vagina with a finger in it.

The tube 100 may be provided with a sealed member 130 and a tight band 140 at the circumference of the closed end part 110.

The tight band 140 provides an adhesion so that the tube 100 wouldn't take off from a finger by an artificial strength.

The sealed member 130 is to seal the open end part 110 when the tube 100 is turned over. In the embodiment the sealed member 130 may be provided as a bundle of string at the circumference of the open end part 110. However, the sealed member 130 may be provided with different sealed structures such as adhesively sealing the open end part 110 by applying glue at the outer surface of the open end part when the tube 100 is turned over or as zip locking the open end part 110.

Meanwhile, the tube 100 may be composed of at least one of a natural rubber, synthetic rubber, or silicon. For example, the tube 100 of the embodiment is provided with a silicon material.

The collecting part 200 may be provided as a pad form that attaches to the outer surface of the closed end part 120 of the tube 100. The collecting part 200 is to collect sample of the cervix, and may be provided with different hypoallergenic forms like brush, cotton, wool, etc. that a cell could stick. Meanwhile, in the collecting part 200, a material that could cause an antigen-antibody reaction and a signal color material that could be seen by a naked eye in reacting to HPV may be comprised.

A turnover member 300 is provided to prevent the collecting part 200 contaminating from the outside contaminants, wherein the collecting part 200 collects intravaginal sample by turning over inside out of the tube 100 and placed inside of the tube 100. In an example, the turner 300 comprises a pull string 310, where the one end of the turner 300 is installed as exposed to the outside through the open end part 110 of the tube 100. The other end of the turner 300 is attached inner side of the closed end part 120 of the tube 100. That is, when the tube 100 is inserted inside of woman's vagina, the collecting part 200 is placed inside of the tube 100 by pulling the pull string 310 as taking out a finger and thereby turning over inside out of the tube 100.

FIGS. 3 to 6 are drawings of the method for self-collecting intravaginal sample by stages using an apparatus for self-collecting intravaginal sample.

The method for self-collecting intravaginal sample comprises an inserting step, a collecting step, a turnover step, and a sealing step.

Figure 3:
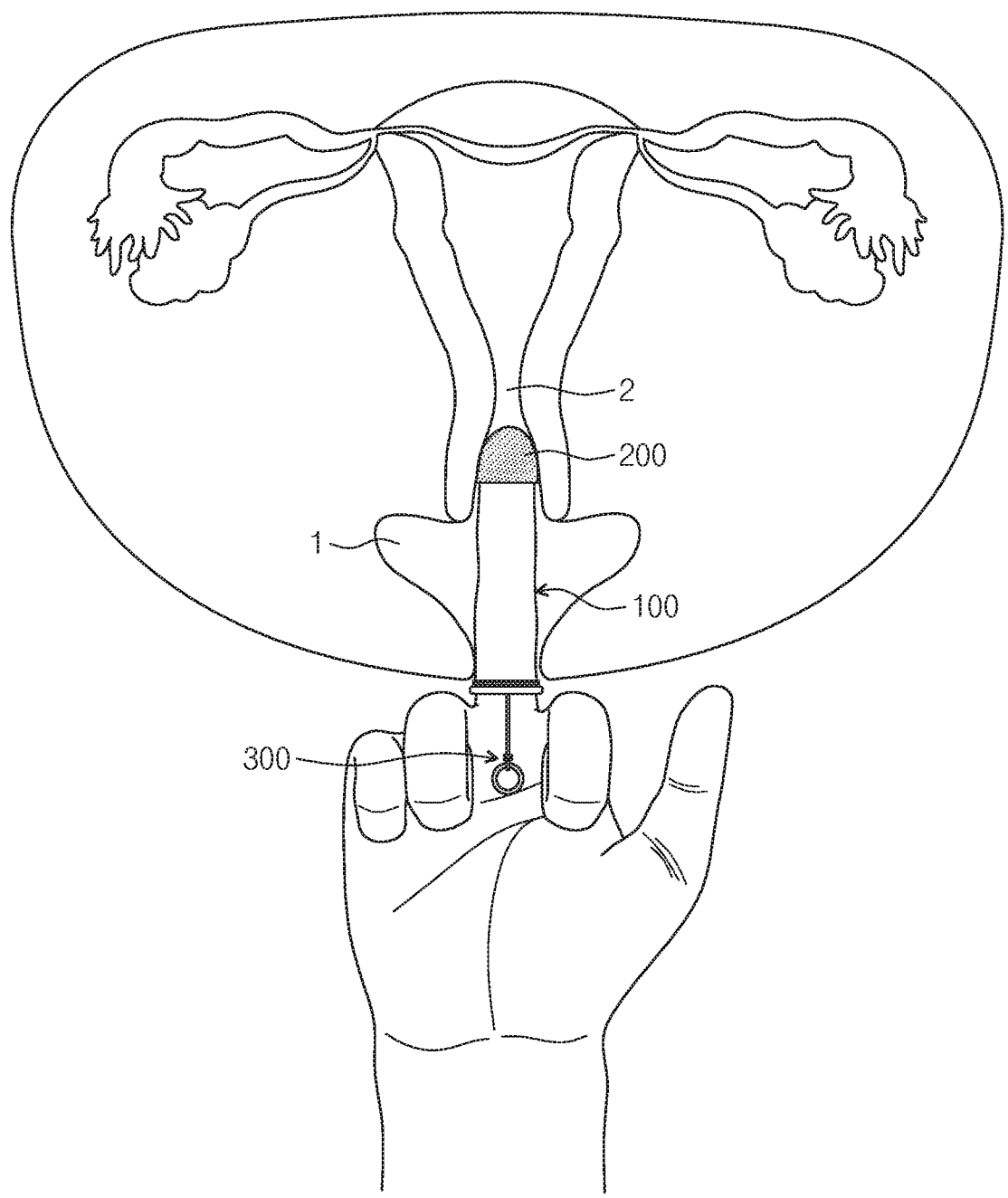
FIGS. 3 to 6 are drawings of the method for self-collecting intravaginal sample by stages using an apparatus for self-collecting intravaginal sample.
Figure 4:
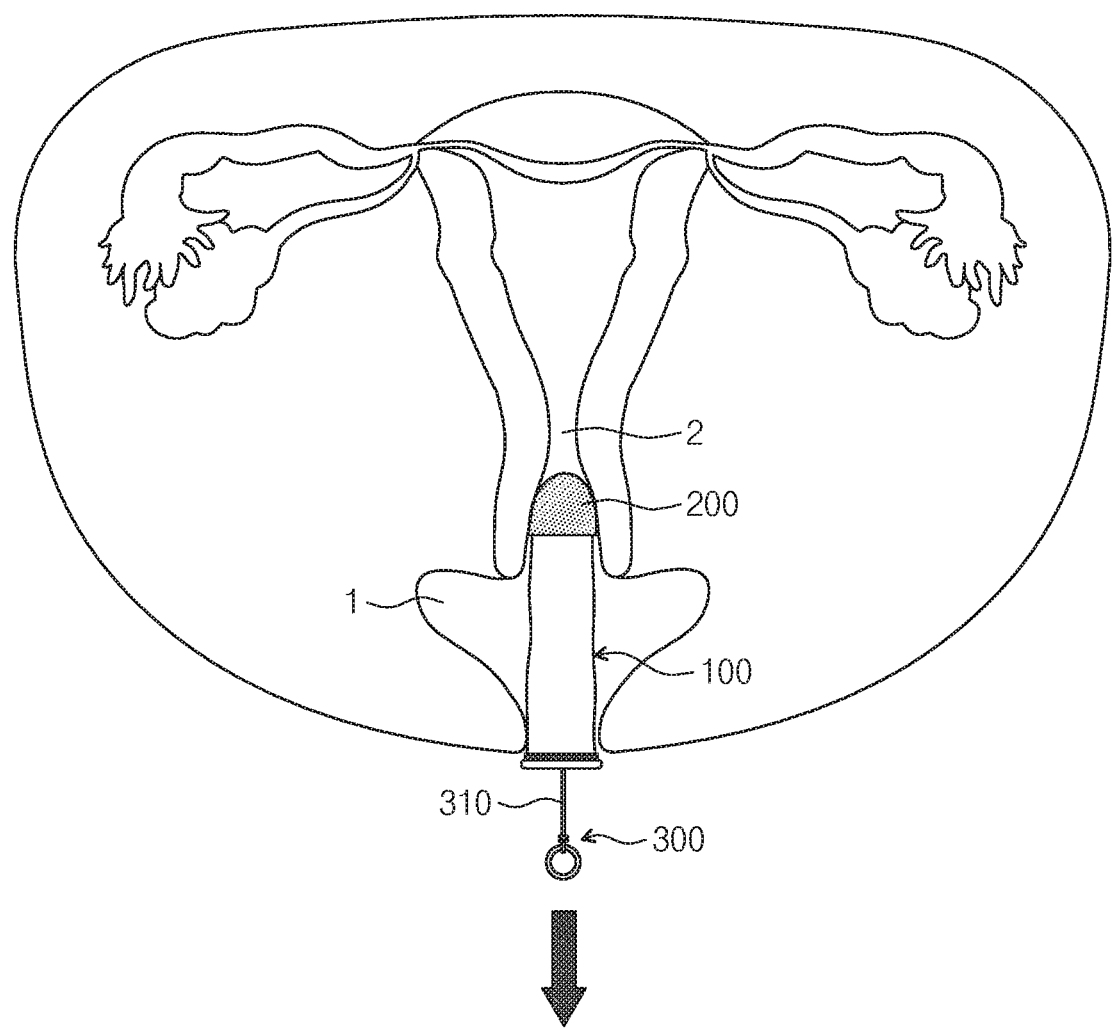
Figure 5:
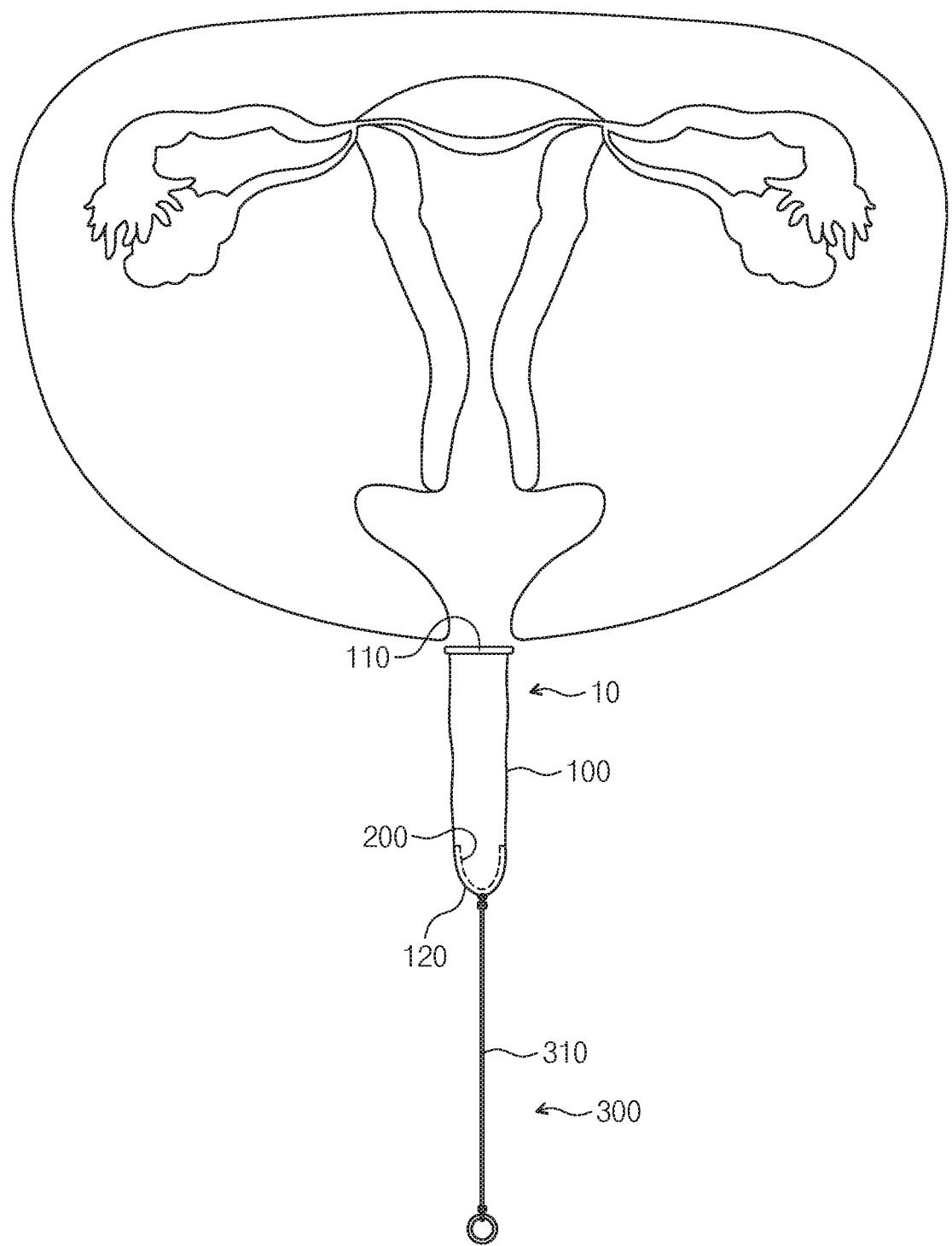

(The inserting step) like FIG. 3, a user places her finger inside the tube 300 and inserts the tube 100 inside of her cervix through her intravaginal 1. (The collecting step) when the closed end part 120 of the tube 100 enters a cervix 2, the woman may collect a sample of the intravaginal to the collecting part 200 using her fingertip, wherein the collecting part 200 is attached at the outer surface of the closed end of the tube 100. (The turnover step) To prevent contaminating the collecting part 200 from outside contaminants, the collecting part 200 is placed inside of the tube 100 by turning over inside out of the tube 100, wherein the collecting part 200 comprises a collected intravaginal sample. Like FIGS. 4 and 5, the turnover step turns over inside out of the tube 100 by pulling the pull string 310 of the turner 300 after taking out the finger from the tube, wherein the tube 100 is inserted inside of the woman's vaginal.

Figure 6:
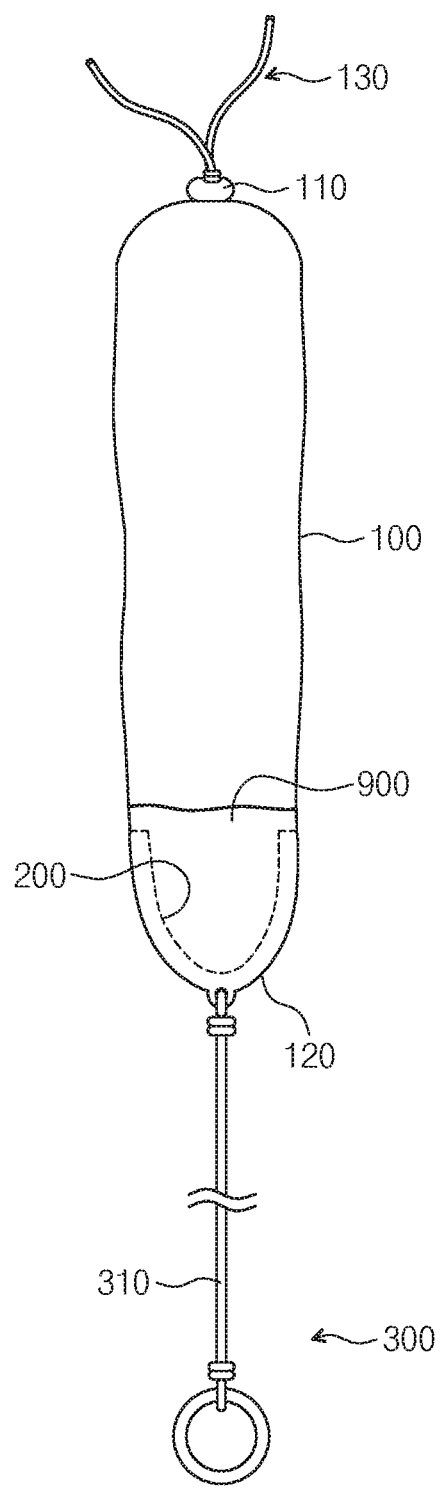

Like FIG. 6, (the sealing step) prevents contaminating the sample by sealing the open end part 110 of the tube 100 after the turnover step. In here, injecting a fixing solution 900 step may be comprised to prevent deformation of the sample of inside of the tube 100 after the turnover step. That is, to test a uterine cervical cancer, the sample should be maintained as alive and therefore should be sealed after injecting the fixing solution inside of the tube 100 where the collected sample is present inside of the collecting part 200. An alcoholic solution or a solution which combines the alcoholic solution and a solution that could optimize a polymerase chain reaction examination result is appropriate for the fixing solution. There are ethanol, methanol, and etc. for alcoholic solution, and there are PBS buffer solution, paraformaldehyde, and etc. for optimizing a polymerase chain reaction examination result.

Like this, an apparatus for self-collecting intravaginal sample 10 has no feeling of irritation as a user uses her finger to insert the tube 100 inside of her cervix through her vagina. Especially, as a user can insert the apparatus by adjusting her finger position depending on her vagina's position, form, and entry angle, the apparatus is useful easily collecting an intravaginal sample and inserting the apparatus inside of her cervix, and may prevent causing a pain by irritating an inner wall of the vagina or damaging the inner wall of the vagina.

A Second Embodiment

Figure 7:
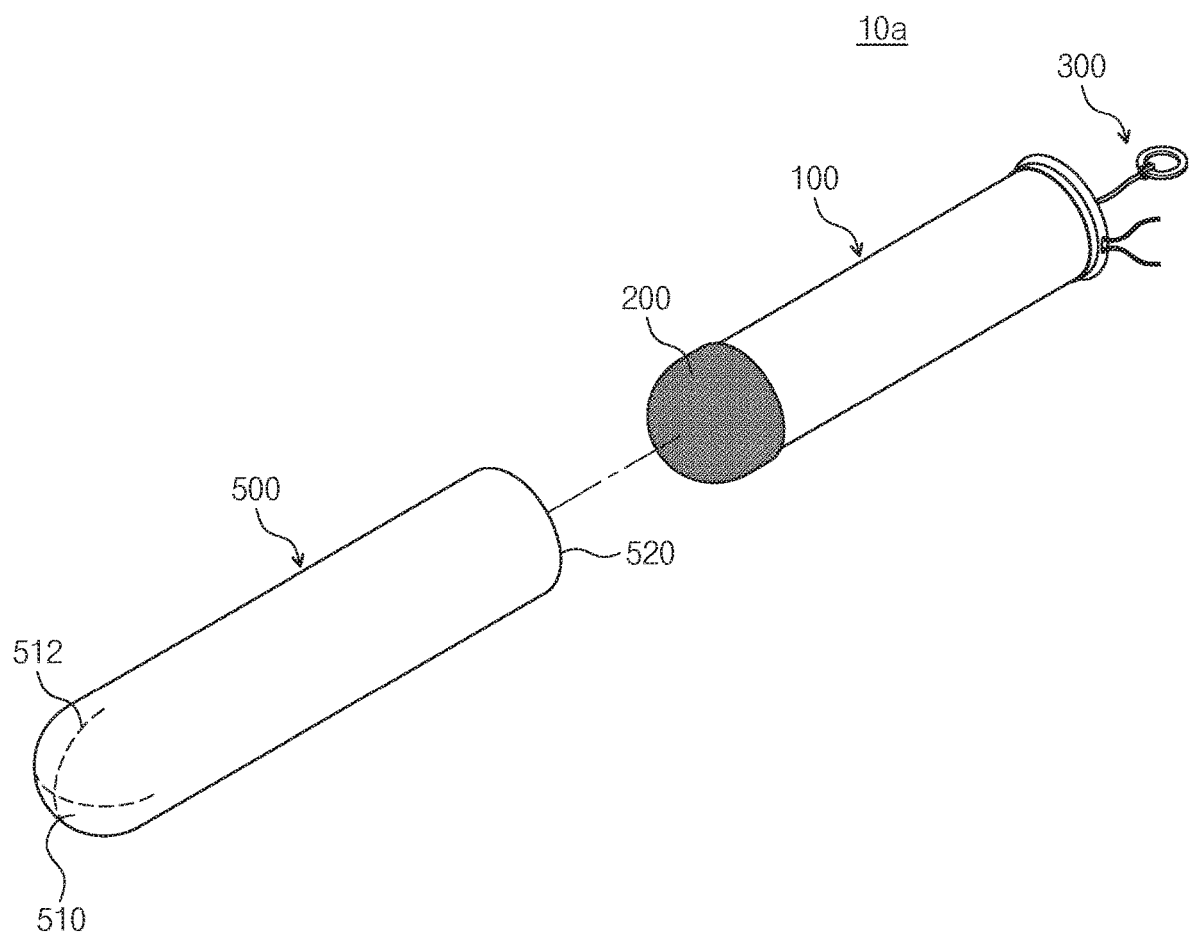
FIG. 7 is a drawing of the second embodiment of the present invention.

FIG. 7 is a drawing according to the second embodiment of the present invention. An apparatus for self-collecting intravaginal sample 10a added a protective cover 500 to prevent contaminating the collecting part 200 while inserting the tube 100 inside of a vagina after inserting a finger in the tube 100. The protective cover 500 may be a cylinder form to cover the tube 100 with the front end is open and the end part is closed. Also, an end part 510 (counterpart of the closed end part of the tube) of the protective cover 500, a tear line 512 is formed to be torn easily. That is, when a user inserts her finger in the tube 100 and inserts the tube 100 inside of her cervix through her vagina, the protective cover 500 protects the collecting part 200. And right before the collecting step, pulling a front end 520 of the protective cover 500 will make the end part of the protective cover 500 to be torn easily by following the tear line 512 and will be removed as taking out the protective cover 500 outside of the vagina.

A Third Embodiment

Figure 8:
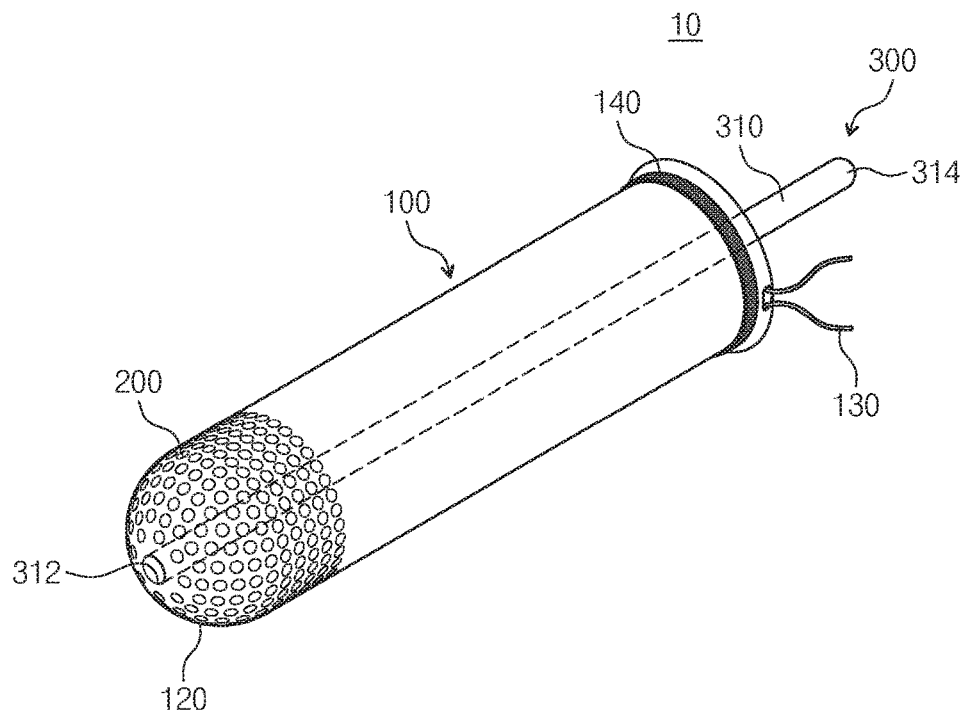
FIG. 8 is a perspective view of an apparatus for self-collecting intravaginal sample in accordance with the third embodiment of the present invention.
Figure 9:
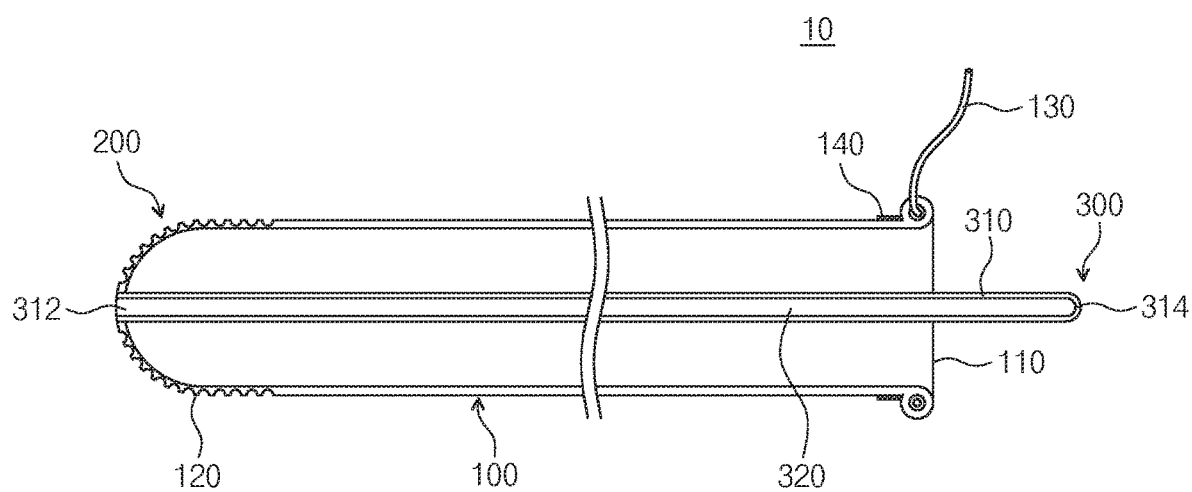
FIG. 9 is a plan view of an apparatus for self-collecting intravaginal sample in accordance with the third embodiment of the present invention.

FIG. 8 is a perspective view of an apparatus for self-collecting intravaginal sample in accordance with the third embodiment of the present invention. FIG. 9 is a plan view of an apparatus for self-collecting intravaginal sample in accordance with the third embodiment of the present invention.

Referring to FIGS. 8 and 9, the apparatus for self-collecting intravaginal sample 10 comprises the tube 100, the collecting part 200, and the turner 300.

The tube 100 has the open end part 110 and the closed end part 120, and provides an inner space where a finger may enter so that the tube can insert inside of woman's vagina. The tube 100 is to pass through passage of an inner side of a vagina so that the closed end part 120 of the tube can reach a cervix. Therefore, the tube 100 may be a cylinder structure that is easily inserted in inner side of vagina with a finger in it.

The tube 100 may be provided with the sealed member 130 and the tight band 140 at the circumference of the closed end part 110.

The tight band 140 provides an adhesion so that the tube 100 wouldn't take off from a finger by an artificial strength.

The sealed member 130 is to seal the open end part 110 when the tube 100 is turned over. In the embodiment the sealed member 130 may be provided as a bundle of string at the circumference of the open end part 110. However, the sealed member 130 may be provided with different sealed structures such as adhesively sealing the open end part 110 by applying glue at the outer surface of the open end part when the tube 100 is turned over or as zip locking the open end part 110.

Meanwhile, the tube 100 may be composed of at least one of a natural rubber, synthetic rubber, or silicon. For example, the tube 100 of the embodiment is provided with silicon material.

The collecting part 200 may be provided as bumpy form that forms at the outer surface of the closed end part 120 of the tube 100. That is, the collecting part 200 may comprise several bumpy forms that form at the outer surface of the closed end part 120. The collecting part 200 is to collect intravaginal sample and may be provided with different forms like bumpy form or groove form that a cell could stick. Meanwhile, in the collecting part 200, a material that could cause an antigen-antibody reaction and a signal color material that could be seen by a naked eye in reacting to HPV may be comprised.

The turner 300 is provided to prevent the collecting part 200 contaminating from the outside contaminants, wherein the collecting part 200 collects intravaginal sample by turning over inside out of the tube 100 and placed inside of the tube 100. Also, the turner 300 provides a flow channel 320 that forms a sample moving route so that the sample may be provided to an apparatus 20 (shown in FIG. 14).

In an example, the turner 300 is provided as a flexible hose 310 that the flow channel 320 is formed. The flexible hose 310 of the turner 300 comprises a flow part 312 and the leak part 314, wherein the flow part 312 is connected to the closed end part 120 of the tube 100 to be contacted, and wherein the leak part 314 exposed to the outside through the open end part 110 of the tube 100. The flow part 312 is opened so that a fixing solution (dilution sample solution) may inflow when the tube 100 is turned over. The leak part 314 is closed to prevent random leakage of the dilution sample solution, and is cut and used before providing the dilution sample solution to the apparatus 20 (shown in FIG. 14).

That is, when the tube 100 is inserted inside of woman's vagina, the collecting part 200 is placed inside of the tube 100 by pulling the turner 300 as taking out a finger and thereby turning over inside out of the tube 100. After that, the fixing solution 900 (shown in FIG. 13) is provided to the apparatus 20 through the flow channel 320 of the turner 300 after injecting the fixing solution 900 in the tube 100 and mixing them together.

FIGS. 10 to 14 are drawing of the method for self-collecting intravaginal sample by stages using an apparatus for self-collecting intravaginal sample.

The method for self-collecting intravaginal sample comprises an inserting step, a collecting step, a turnover step, a fixing solution injecting step, a sealing step, and a dilution sample solution providing step.

Figure 10:
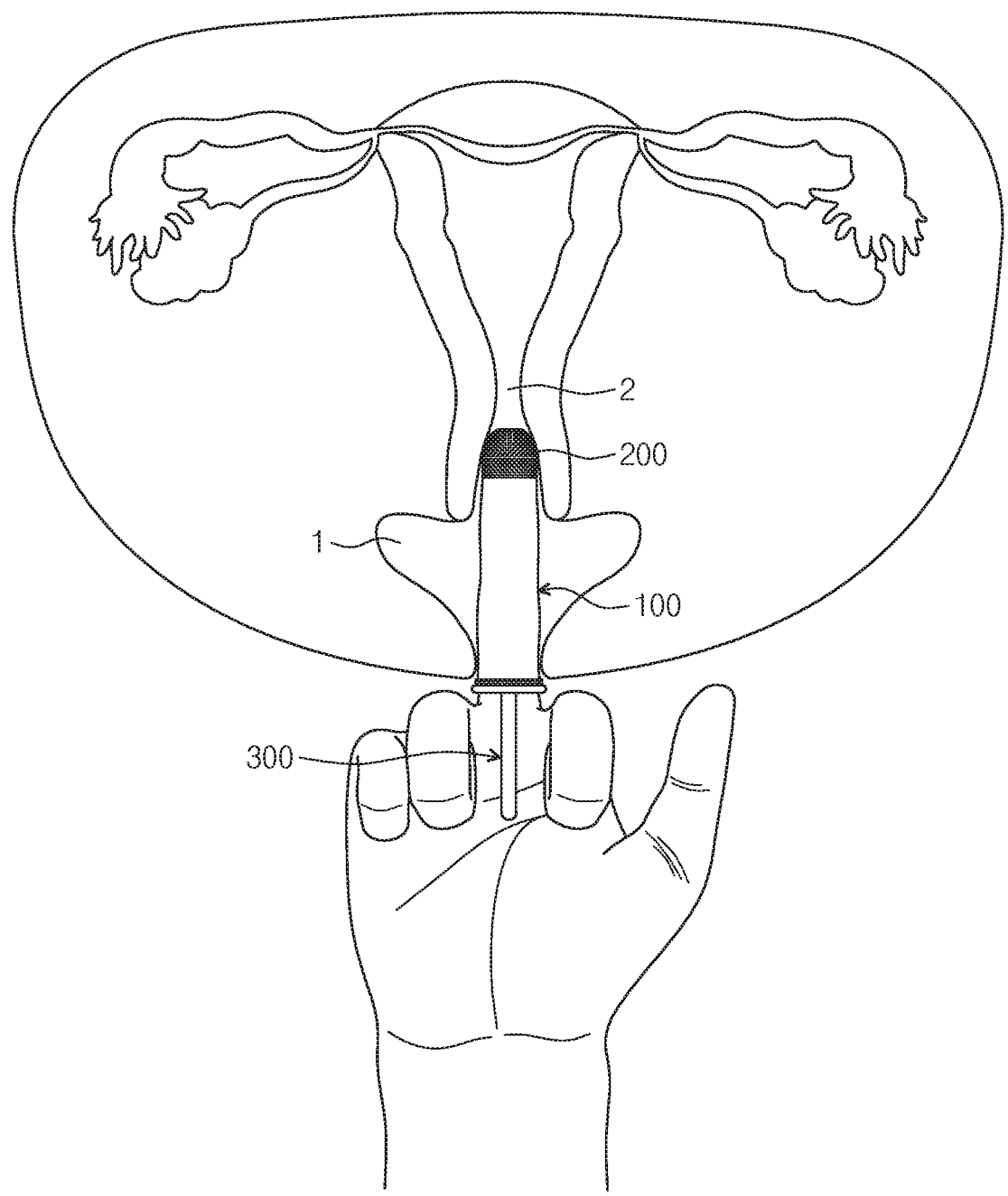
FIGS. 10 to 14 are drawing of the method for self-collecting intravaginal sample by stages using an apparatus for self-collecting intravaginal sample.

(The inserting step) like FIG. 10, a user places her finger inside the tube 300 and inserts the tube 100 inside of her cervix through her intravaginal 1. (The collecting step) when the closed end part 120 of the tube 100 enters a cervix 2, the woman may collect a sample of the intravaginal to the collecting part 200 using her fingertip, wherein the collecting part 200 is attached at the outer surface of the closed end of the tube 100. (The turnover step) the collecting part 200 places inside of the tube 100 by pulling the turner 300 and thereby turning over inside out of the tube 100. Therefore, the collecting part 200 may be prevented from contamination from outside contaminants, wherein the collecting part 200 has collected intravaginal sample.

Figure 11:
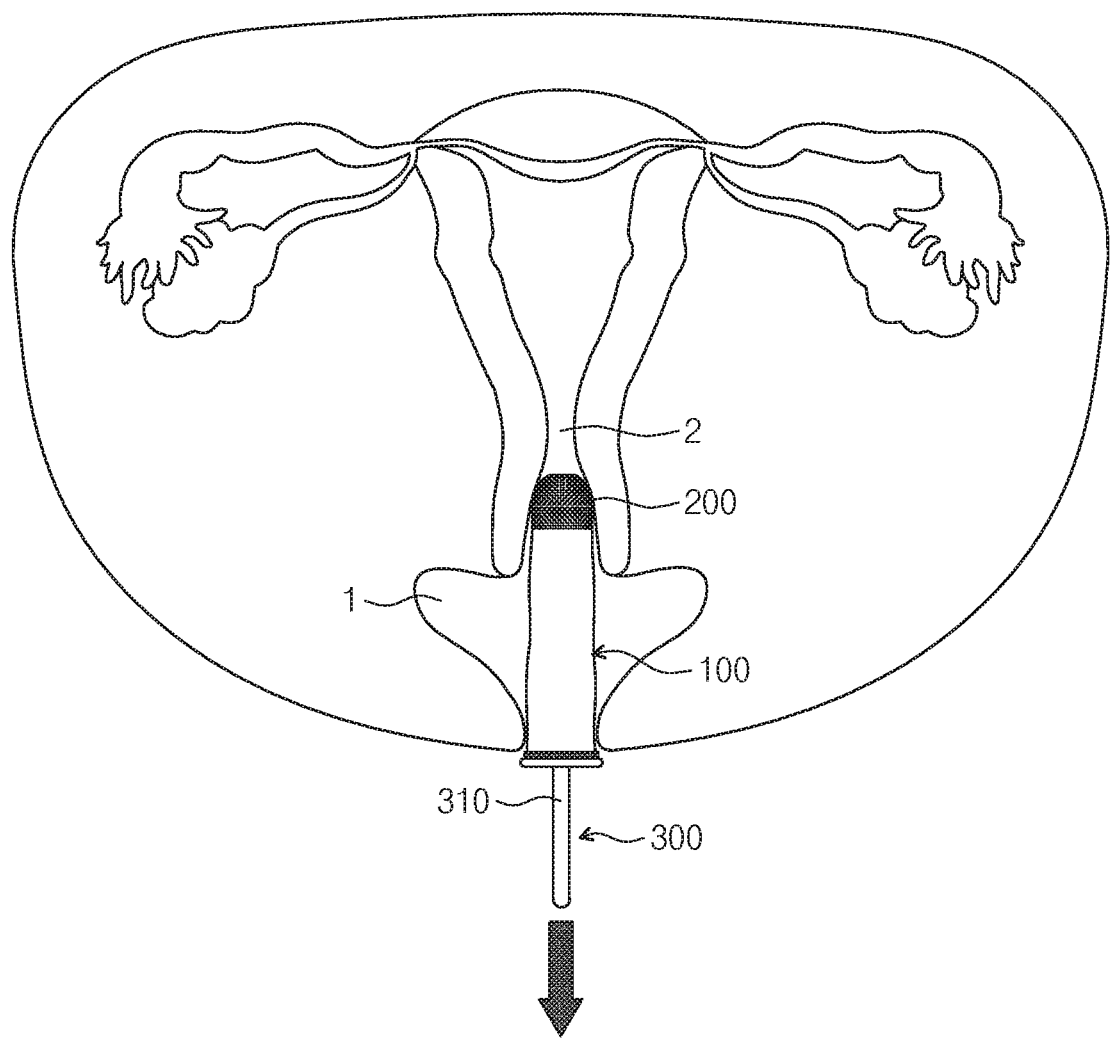
Figure 12:
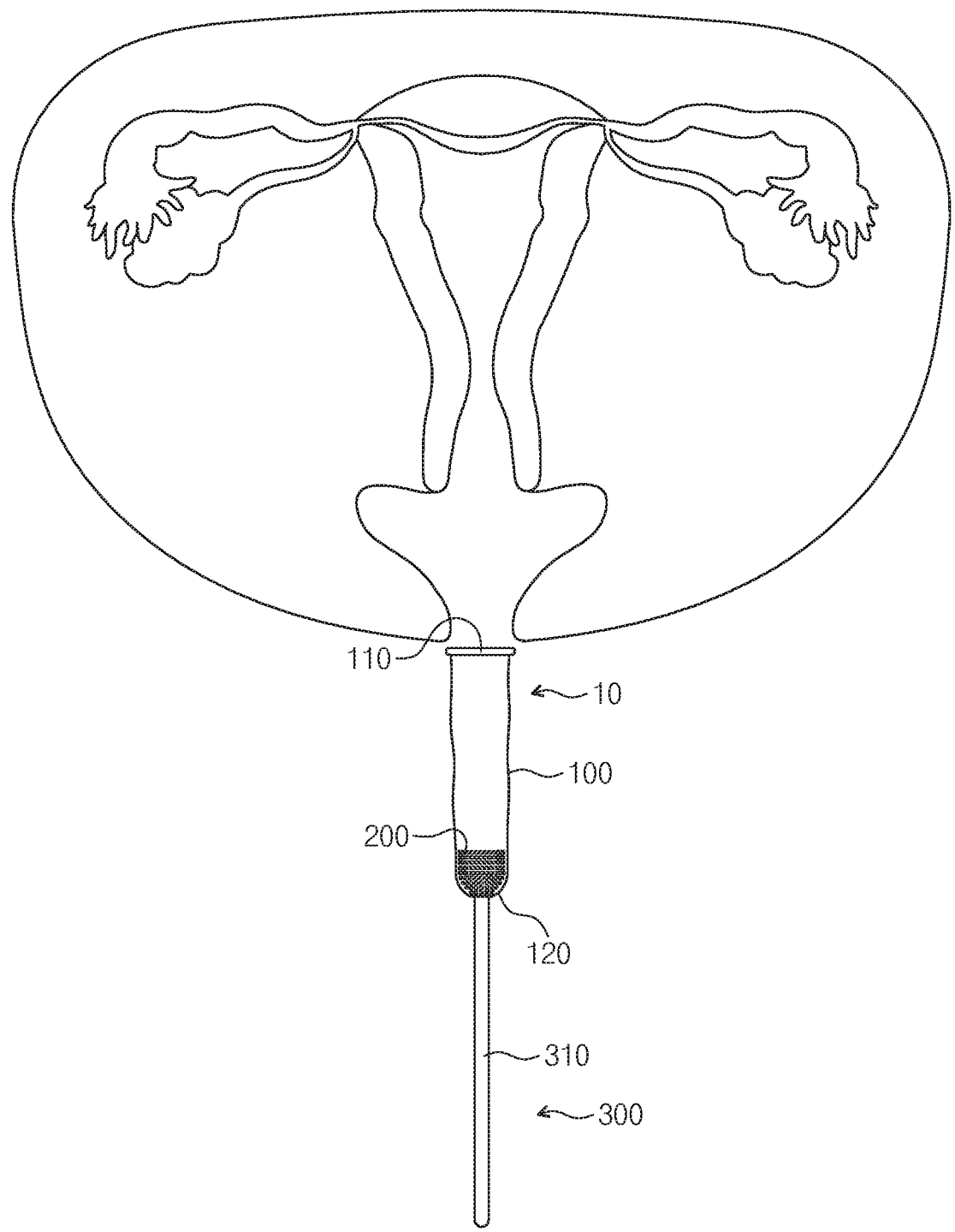

Like FIGS. 11 and 12, the turnover step turns over inside out of the tube 100 by pulling the turner 300 after taking out the finger from the tube, wherein the tube 100 is inserted inside of the woman's vaginal.

Figure 13:
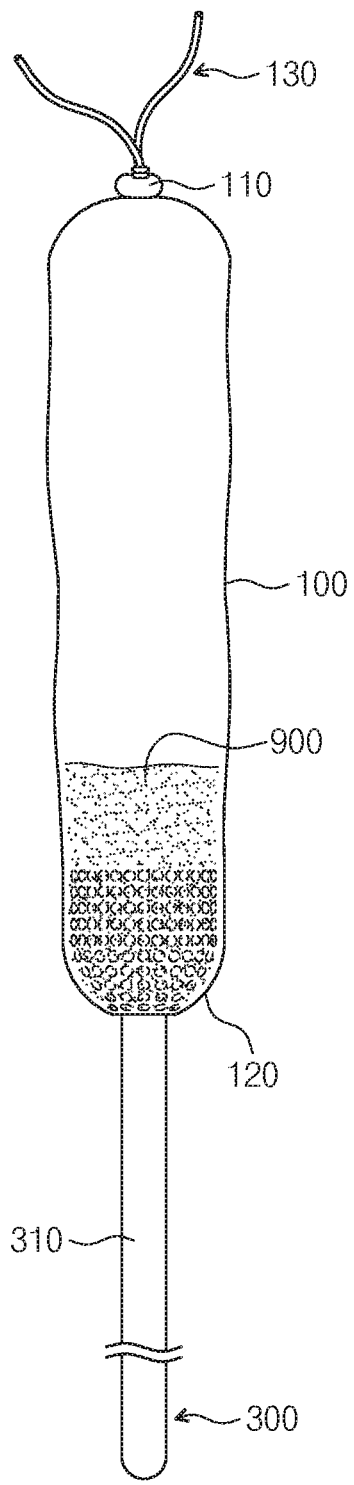

Like FIG. 13, the fixing solution injecting step injects the fixing solution 900 to the inside of the tube 100. The fixing solution 900 is injected inside of the tube 100 to prevent deformation of a sample and to easily provide the sample to the apparatus 20. After the fixing solution is injected, a sample is prevented from contamination by sealing the open end part 110 of the tube 100. For reference, an alcoholic solution or a solution which combines the alcoholic solution and a solution that could optimize a polymerase chain reaction examination result is appropriate for the fixing solution. There are ethanol, methanol, and etc. for alcoholic solution, and there are PBS buffer solution, paraformaldehyde, and etc. for optimizing a polymerase chain reaction examination result.

Figure 14:
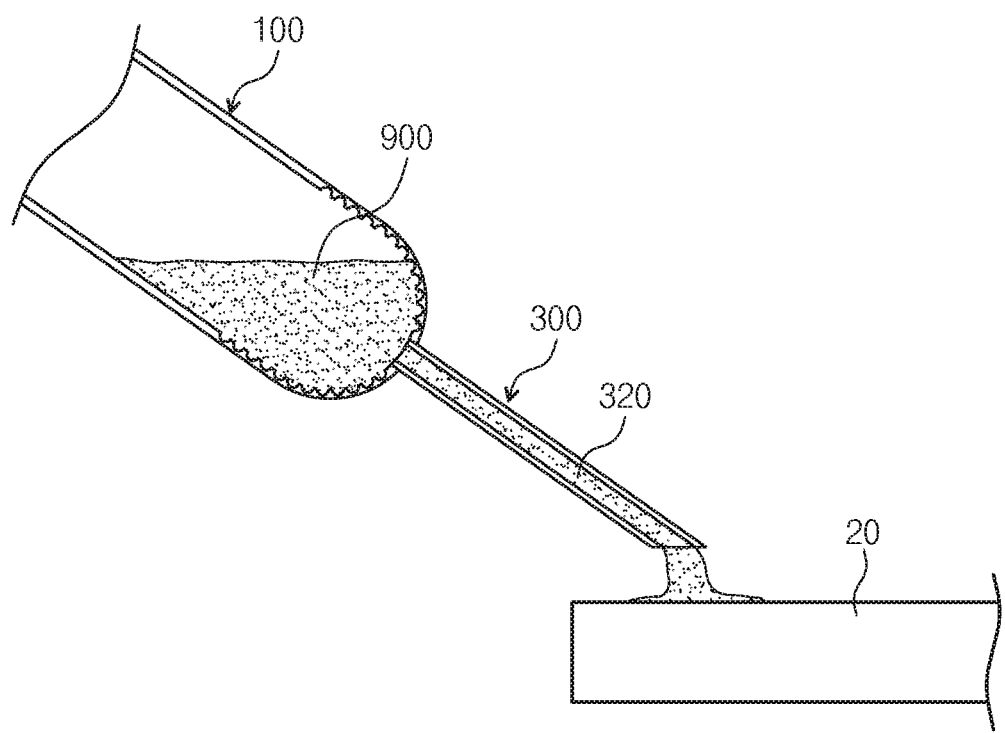

Like FIG. 14, the leak part 314 of the turner is cut and in the dilution sample solution providing step, the dilution sample solution inside of the tube 100 is leaked through the flow channel 320 of the turner. This leaked dilution sample solution may be easily provided to the apparatus 20.

Like this, the apparatus for self-collecting intravaginal sample 10 has no feeling of irritation as a user uses her finger to insert the tube 100 inside of her cervix through her vagina.

Especially, as a user can insert the apparatus by adjusting her finger position depending on her vagina's position, form, and entry angle, the apparatus is useful easily collecting an intravaginal sample and inserting the apparatus inside of her cervix, and may prevent causing a pain by irritating an inner wall of the vagina or damaging the inner wall of the vagina.

Also, contamination of a sample may be minimized when providing the sample from the apparatus for self-collecting intravaginal sample 10 to the apparatus 20, because the apparatus for self-collecting intravaginal sample 10 can easily provide the fixing solution (dilution sample solution) to the apparatus 20 through the flow channel 320 of the turner 300, wherein the fixing solution is mixed with a cell sample.

A Fourth Embodiment

Figure 15:
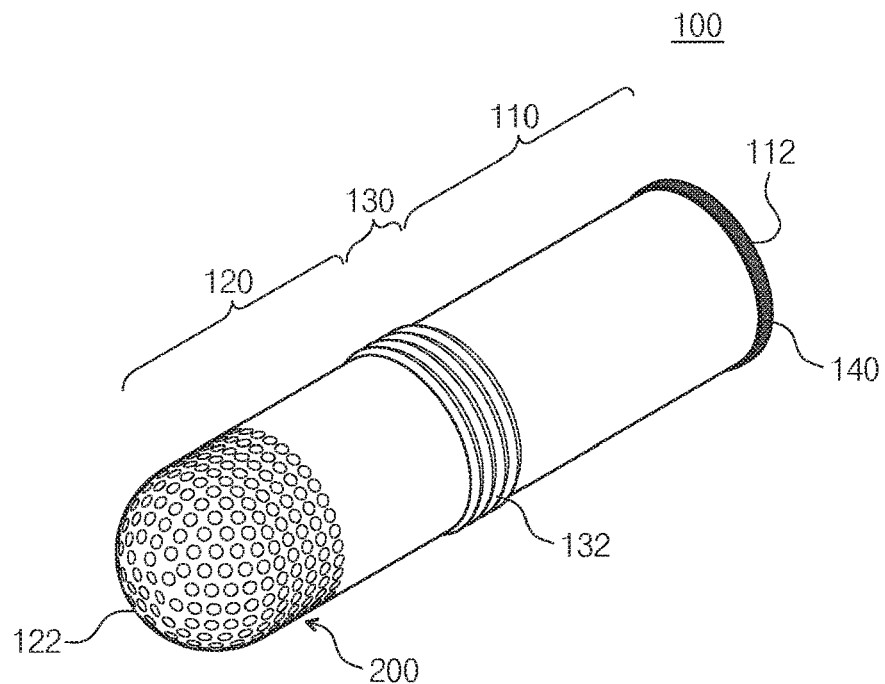
FIG. 15 is a perspective view of an apparatus for self-collecting intravaginal sample in accordance with the fourth embodiment of the present invention.
Figure 16:
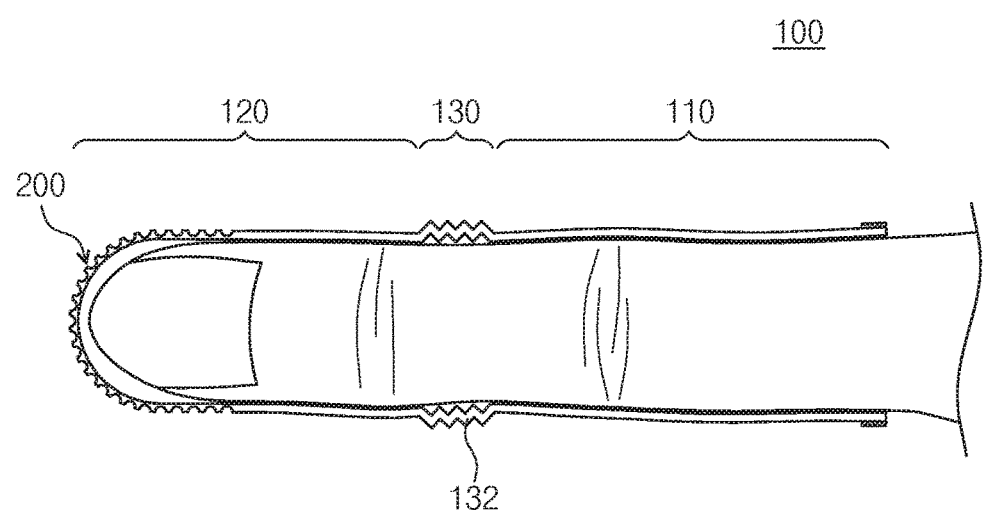
FIG. 16 is a plan view of an apparatus for self-collecting intravaginal sample in accordance with the fourth embodiment of the present invention.
Figure 17:
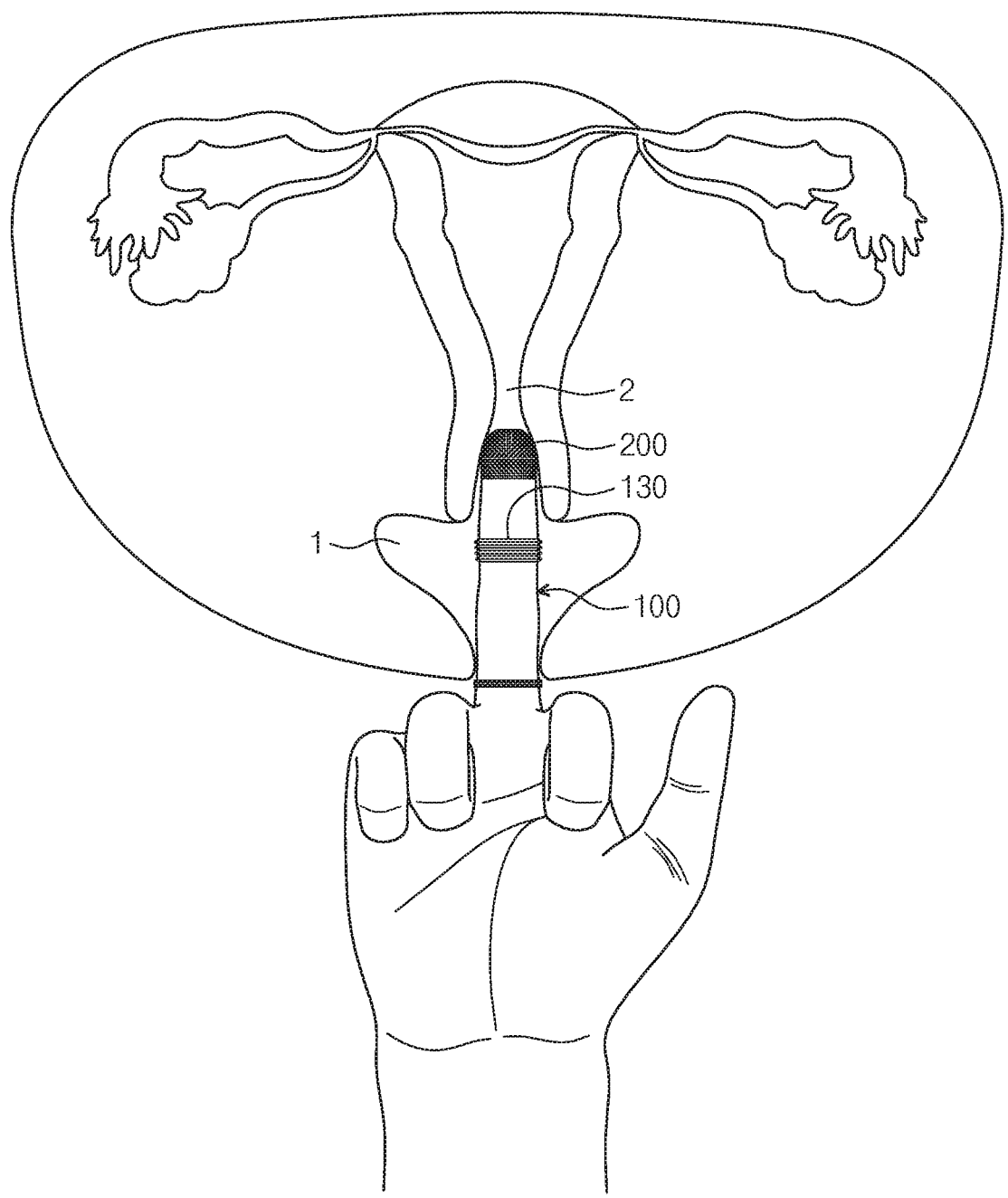
FIGS. 17 and 18 are drawings of an explanation of the method for self-collecting intravaginal sample by using an apparatus for self-collecting intravaginal sample.

FIG. 15 is a perspective view of an apparatus for self-collecting intravaginal sample in accordance with the fourth embodiment of the present invention. FIG. 16 is a plan view of an apparatus for self-collecting intravaginal sample in accordance with the fourth embodiment of the present invention.

Referring to the FIGS. 15 and 16, the apparatus for self-collecting intravaginal sample 10 comprises the tube 100 and the collecting part 200.

The tube 100 may comprise the latter end 110 having the open end part 112, the front end 120 having the closed end part 122, and an extension part 130 in between. The tube 100 provides an inner space that a finger could enter to insert a apparatus into women's vagina. The tube 100 is to pass through a passage of an inner side of a vagina so that the closed end part 120 of the tube can reach a cervix. Therefore, the tube 100 may be a cylinder structure that is easily inserted in inner side of vagina with a finger in it.

Figure 19:
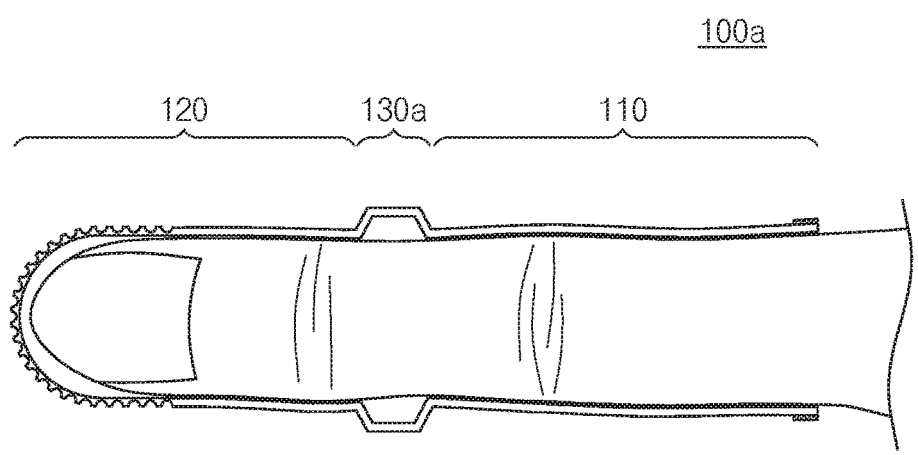
FIG. 19 is a drawing of a modification exemplary of the present invention.

The extension part 130 is formed in between the latter end 110 and the front end 120 so that only the front end 120 may turnover when taking out a finger. The extension part 130 may be provided as there is no friction with a finger. In an example, the extension part 130 comprises at least one wrinkle 132. Also, the extension part 130 is appropriate to have wider cross-section area than the front end 120. Also, the extension part 130 is appropriate to be provided with certain distance with the finger. In another example, like FIG. 19, an extension part 130a may be formed with wide cross-section area to be not contacted with the finger.

For reference, the front end 120 is appropriate to have relatively much flexibility and higher friction than the extension part 130 so that it will turnover easily when taking out a finger. That is, the front end 120 may be formed covering a fingertip tightly.

As described above, when taking out the finger where the tube 100 is inserted in woman's vagina, the tube 100 is overturned to the closed end part 122 of the front end 120 starting from a boundary of the extension part 130 and the front end 120. A reason for that is the front end 120 has a strong friction because it is adhere to skin of the finger and the extension part has a minimal friction because it is separated from the skin of the finger.

Meanwhile, the tube 100 may be provided with the tight band 140 in circumference of the latter part 110. The tight band 140 provides an adhesion so that the tube 100 wouldn't take off from a finger by an artificial strength.

The tube 100 may be composed of at least one of a natural rubber, synthetic rubber, or silicon. In an example, the tube 100 of the embodiment is provided with a silicon material. In another example, the extension part 130 and the frond end 120 may be composed of different material.

The collecting part 200 may be provided as bumpy form that forms at the outer surface of the front end 120 of the tube 100. That is, the collecting part 200 may comprise several bumpy forms that form at the outer surface of the front end 120 of the tube 100. The collecting part 200 is to collect intravaginal sample and may be provided with different forms like bumpy form or groove form that a cell could stick. Meanwhile, in the collecting part 200, a material that could cause an antigen-antibody reaction and a signal color material that could be seen by a naked eye in reacting to HPV may be comprised. In another example, the collecting part 200 may be provided as a pad form that attaches to the outer surface of the closed end part 120 of the tube 100. The collecting part 200 is to collect sample of the cervix, and may be provided with different hypo-allergenic forms like brush, cotton, wool, etc. that a cell could stick.

The method apparatus for self-collecting intravaginal sample using the apparatus for self-collecting intravaginal sample comprising above descriptions is like below.

The method for self-collecting intravaginal sample comprises an inserting step, a collecting step, a turnover step, and a sealing step.

Figure 18:
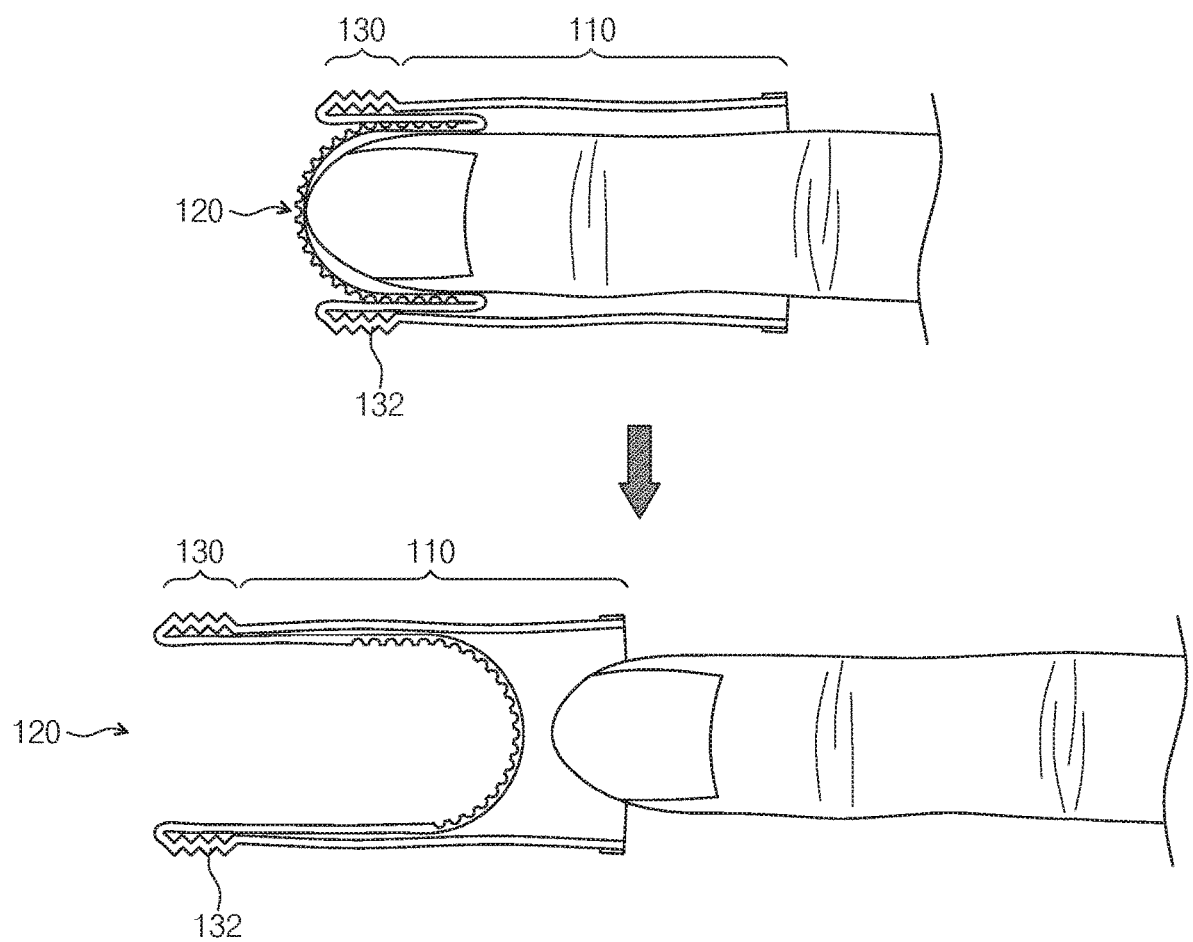

(The inserting step) like FIG. 3, a user places her finger inside the tube 300 and inserts the tube 100 inside of her cervix through her intravaginal 1. (The collecting step) when the closed end part 120 of the tube 100 enters a cervix 2, the woman may collect a sample of the intravaginal to the collecting part 200 using her fingertip, wherein the collecting part 200 is attached at the outer surface of the closed end of the tube 100. (The turnover step) when taking out a finger from the tube 130 which is inserted inside of woman's vagina, the front end 120 of the extension part 130 overturns on the basis of the extension part 130 and the collecting part 200 places inner side of the tube 100 (reference, FIG. 18). Therefore, the collecting part 200 may be prevented from contamination from outside contaminants, wherein the collecting part 200 has collected intravaginal sample.

After the turnover step, a sample maybe prevented from contamination by sealing the extension part 130 of the tube 100. In here, a step injecting the fixing solution to overturned front end 120 may be comprised to prevent deformation of the sample after the turnover step. That is, to test a uterine cervical cancer, the sample should be maintained as alive and therefore should be sealed after injecting the fixing solution inside of the front end 120 where the collected sample is present inside of the collecting part 200. An alcoholic solution or a solution which combines the alcoholic solution and a solution that could optimize a polymerase chain reaction examination result is appropriate for the fixing solution. There are ethanol, methanol, and etc. for alcoholic solution, and there are PBS buffer solution, paraformaldehyde, and etc. for optimizing a polymerase chain reaction examination result.

Like this, an apparatus for self-collecting intravaginal sample 10 has no feeling of irritation as a user uses her finger to insert the tube 100 inside of her cervix through her vagina.

Especially, as a user can insert the apparatus by adjusting her finger position depending on her vagina's position, form, and entry angle, the apparatus is useful easily collecting an intravaginal sample and inserting the apparatus inside of her cervix, and may prevent causing a pain by irritating an inner wall of the vagina or damaging the inner wall of the vagina.

Described explanations indicate implementation form of the present invention and may be changed or corrected within the equal scope of the disclosed explanation and/or inventive concept or those skilled in art. Therefore, detailed descriptions of the present invention do not intend to limit the scope of the inventive concept but is to explain the present invention. Also, attached scope of claims may be understood to include other implementations.

What is claimed is:

1. An apparatus for self-collecting an intravaginal sample comprising:
    a tube providing an inner space that a finger could enter to insert the apparatus into a user's vagina and comprising:
        a latter end having an open end part and a front end having a closed end part,
        a sealing member provided at the latter end around the circumference of the open end part, and
        a tight band provided at the latter end around the circumference of the open end part;
    a collecting part that collects a sample from the vagina, wherein the collecting part is provided at an outer surface of the closed end part of the tube; and
    a turner comprising a first end attached to an inner surface of the closed end part of the tube and a second end provided as exposed to the outside of the inner space through the open end part of the tube, wherein the turner turns the tube inside out so that the collecting part which collects the sample from the vagina is then positioned inside of the tube to prevent the collecting part being contaminated from an outer contaminant,
    wherein the turner comprises a flexible hose in which a flow channel is formed between the first end and the second end of the turner, the flow channel forms a sample-moving path for the sample to be provided to a diagnosis apparatus,
    wherein the flexible hose connects to the inner surface of the closed end part of the tube at the first end of the turner,
    wherein the first end of the of the turner comprises an opening at an outer surface of the closed end part of the tube, wherein the opening is arranged such that the sample inflows into the sample-moving path of the flow channel when the tube is pulled inside out.

2. The apparatus of claim 1, wherein the collecting part further comprises a bumpy surface which is formed at the outer surface of the closed end part of the tube.

3. The apparatus of claim 1, wherein the tube further comprises an extension part which prevents friction between a finger and the tube so that the front end may turn inside out when taking out the finger, and wherein the extension part is positioned in between the front end and the latter end.

4. The apparatus of claim 3, wherein a cross section area of the extension part is larger than a cross-section area of the front end.

5. The apparatus of claim 3, wherein the extension part has at least one preformed wrinkle.

6. The apparatus of claim 3, wherein the front end has a relatively higher flexibility and elasticity than the extension part.

7. The apparatus of claim 1, wherein the tube is composed of at least one of natural rubber, synthetic rubber, and silicon.

8. The apparatus of claim 1, wherein the apparatus for self-collecting intravaginal sample further comprises a protective cover which encases the tube and protects the collecting part from the outer contaminant when it is inserted inside of the women's vagina, wherein a tear line is formed at a closed end part of the protective cover.

9. A method for self-collecting intravaginal sample comprising:
- inserting a finger in a tube which comprises an open end part and closed end part, and then inserting the tube into a user's vagina;
- collecting a sample from the user's vagina using a collecting part which is attached an outer surface of the closed end part of the tube by using the finger that is inserted in the tube;
- after the sample has been collected, turning the tube inside out with a turner extending between a first end and a second end and comprising a flow channel, by pulling the second end of the turner after taking out the finger, while maintaining the tube in the user's vagina, to place the collecting part inside of the tube and to prevent contaminating the collecting part from outside contaminants,
- wherein the first end of the turner is attached to an inner surface of the closed end part of the tube,
- wherein the second end of the turner is provided as exposed to the outside of the inner space through the open end part of the tube; and
- moving the sample via the flow channel, wherein the flow channel forms a sample-moving path for the sample to be provided to a diagnosis apparatus,
- wherein the first end of the turner comprises an opening at an outer surface of the closed end part of the tube at the first end of the turner, wherein the opening is arranged such that the sample inflows into the sample-moving path of the flow channel when the tube is pulled inside out,
- wherein the method further comprises:
  - an injecting step of injecting a fixing solution inside of the tube to prevent deterioration of the sample after the turnover step; and
  - a sealing step of sealing the open end part of the tube after the turnover step.

10. The method of claim 9, wherein the collecting part comprises a signal color material that could be identified by the naked eye in reacting to human papilloma virus (HPV).

* * * * *